United States Patent
Schaub et al.

(10) Patent No.: US 12,172,953 B2
(45) Date of Patent: Dec. 24, 2024

(54) PROCESS FOR THE PRODUCTION OF ACETALS FROM CARBON DIOXIDE

(71) Applicants: BASF SE, Ludwigshafen am Rein (DE); Ruprecht-Karls-Universität Heidelberg, Heidelberg (DE)

(72) Inventors: Thomas Schaub, Ludwigshafen (DE); Ivana Jevtovikj, Heidelberg (DE); A. Stephen K. Hashmi, Heidelberg (DE); Kohei Sekine, Heidelberg (DE)

(73) Assignees: BASF SE, Ludwigshafen am Rhein (DE); Ruprecht-Karis-Universität Heidelberg, Heidelberg (DE)

( * ) Notice: Subject to any disclaimer, the term of this patent is extended or adjusted under 35 U.S.C. 154(b) by 559 days.

(21) Appl. No.: 17/425,805

(22) PCT Filed: Feb. 5, 2020

(86) PCT No.: PCT/EP2020/052838
§ 371 (c)(1),
(2) Date: Jul. 26, 2021

(87) PCT Pub. No.: WO2020/161175
PCT Pub. Date: Aug. 13, 2020

(65) Prior Publication Data
US 2022/0119332 A1    Apr. 21, 2022

(30) Foreign Application Priority Data
Feb. 6, 2019 (EP) .................................... 19155759

(51) Int. Cl.
*C07C 41/50* (2006.01)
*B01J 31/18* (2006.01)
*B01J 31/22* (2006.01)
*B01J 31/24* (2006.01)

(52) U.S. Cl.
CPC ............ *C07C 41/50* (2013.01); *B01J 31/185* (2013.01); *B01J 31/2252* (2013.01); *B01J 31/2295* (2013.01); *B01J 31/2404* (2013.01); *B01J 31/2409* (2013.01); *B01J 2531/821* (2013.01)

(58) Field of Classification Search
CPC ....................................................... B01J 41/50
See application file for complete search history.

(56) References Cited

PUBLICATIONS

Chen, Y. L. et al. "(6R,8S)-(2-Benzimidazolyl)hydroxymethylpenicillanic acids as potent antibacterial agents and β-lactamase inhibitors" Journal of Antibiotics (1991), 44(8), 870-84 (Year: 1991).*
Schieweck, B. G. et al. "Tailor-made Molecular Cobalt Catalyst System for the Selective Transformation of Carbon Dioxide to Dialkoxymethane Ethers" Angew. Chem. Int. Ed. 2017, 56, 10854-10857 (Year: 2017).*
International Search Report for International Application No. PCT/EP2020/052838 mailed May 4, 2020, 2 pgs.
Max Siebert et al: "Selective Ruthenium-Catalyzed Transformation of Carbon Dioxide: An Alternative Approach toward Formaldehyde", Journal of the American Chemical Society, vol. 141, No. 1, Dec. 9, 2018 (Dec. 9, 2018), pp. 334-341.
Katharina Thenert et al, "Ruthenium-Catalyzed Synthesis of Dialkoxymethane Ethers Utilizing Carbon Dioxide and Molecular Hydrogen", Angewandte Chemie, International Edition, vol. 55, No. 40, Sep. 1, 2016 (Sep. 1, 2016), p. 12266-12269.
Denticity, Wikipedia, "https//en.wikipedia.org/wiki/Denticity", retrieved Jul. 22, 2024, 3 pgs.
Tetrakis(triphenylphosphine)palladium(0), Wikipedia, "https://de.wikipedia.org/wiki/Tetrakis(triphenylphosphin)palladium(0)", retrieved Jul. 22, 2024, 4 pgs.

* cited by examiner

*Primary Examiner* — Medhanit W Bahta
(74) *Attorney, Agent, or Firm* — Grüneberg and Myers PLLC

(57) ABSTRACT

The invention relates to a process for the preparation of acetals from carbon dioxide. The invention also relates to a mixture of phosphorus containing ligands comprising least one polydentate ligand and at least one monodentate ligand. Further, the invention also relates to the use of mixtures comprising at least one polydentate ligand and at least one monodentate ligand in transition metal complexes for the preparation of acetals.

25 Claims, No Drawings

PROCESS FOR THE PRODUCTION OF ACETALS FROM CARBON DIOXIDE

FIELD OF THE INVENTION

The invention relates to a process for the preparation of acetals from carbon dioxide. The invention also relates to a mixture of phosphorus containing ligands comprising at least one polydentate ligand and at least one monodentate ligand. Further, the invention also relates to the use of mixtures comprising at least one polydentate ligand and at least one monodentate ligand in transition metal complexes for the preparation of acetals.

BACKGROUND OF THE INVENTION

Dialkoxymethanes or acetals of formaldehyde, in particular dimethoxymethane, are of particular commercial interest. Since they are able to increase the octane number, lower soot and $NO_x$ formation, they are attractive candidates for the use as a gasoline-additive. In addition, acetals are valuable compounds for the pharmaceutical or cosmetics industries too. Acetals of formaldehyde can serve, inter alia, as solvent for the preparation of pharmaceutical or cosmetic compounds. Therefore, new and simple processes for the production of said acetals are urgently sought after. In order to minimize production costs the processes should be, particularly highly active as well as highly selective for the formation of the desired acetals.

The acetals of formaldehyde are usually produced by oxidation of an alcohol or the reaction of formaldehyde with the corresponding alcohol. Formaldehyde itself is produced by the oxidation of methanol.

An alternative method to produce the acetals of formaldehyde is the direct reduction of carbon dioxide with hydrogen in the presence of the corresponding alcohol using transition metal catalysts and Lewis acidic co-catalyst.

Angewandte Chemie International Edition, 2016, DOI: 10.1002/anie.201606427 and Angewandte Chemie International Edition, 2017, DOI: 10.1002/anie.201702905 describe the synthesis of dimethoxymethane by a multistep reaction starting from carbon dioxide, hydrogen and methanol using the catalyst [Ru(triphos)(tmm)] or [Co(triphos)] (triphos: 1,1,1-tris(diphenylphosphinomethyl)ethane, tmm: trimethylene methane) in combination with a Lewis acidic co-catalyst e.g. $Al(OTf)_3$ or $HNTf_2$ (Tf: triflate). Dimethoxymethane (DMM) has been formed with a turnover number (TON) of 71. It has been investigated that a higher loading of the catalyst results in a lower TON of DMM. However, a lower loading of the catalyst results in an increased TON for DMM. Likewise the turnover number of the side product methyl formate (MF) will increase.

Journal of the American Chemical Society, 2018, DOI: 10.1021/jacs.8b10233 discloses an active catalyst system to obtain the acetale dimethoxymethane from $CO_2$, $H_2$ and methanol in the presence of a ruthenium-catalyst with the tridentate phosphine ligand tris(diphenylphsophinomethylene)amine in combination with $Al(OTf)_3$ as co-catalyst, whereby high turnover numbers can be achieved. However, the selectivity remains low, as the by-product methylformate is formed at the same time with high TON. A higher selectivity to the dimethoxymethane could only be obtained at significant lower catalyst activities.

Currently, high catalyst activities are only obtained at a low selectivity towards the desired product. Thus, the processes of prior art are uneconomic, as the unwanted methyl formate must be separated from the product and yield in losses of methanol due to the formation of the by-product. Therefore, high activities of the catalyst system as well as selectivity of the reaction for the acetals are desired to minimize production costs.

Accordingly, it is an object of the invention to overcome these disadvantages. In particular, it is an object of the invention to provide an optimized catalyst system in order to obtain the desired acetals with high activities but only with a low amount of side products, such as formates.

The problem underlying of the invention is solved by a process, wherein carbon dioxide and hydrogen are reacted with at least one alcohol compound in the presence of a transition metal catalyst complex, comprising at least one polydentate ligand, at least one monodentate ligand, and a Lewis acid.

SUMMARY OF THE INVENTION

The invention relates to a process for the production of a compound of the formula (I)

wherein
each $R^1$ is independently from each other selected from $C_1$-$C_{40}$ alkyl, which is unsubstituted or substituted with 1, 2, 3, 4 or 5 substituents selected from OH, halogen, $C_1$-$C_6$ alkoxy or $C_6$-$C_{20}$ aryl;
or both $R^1$ form together a divalent bridging group $R^2$ selected from linear $C_2$-$C_9$-alkanediyl, wherein the alkanediyl is unsubstituted or substituted by 1, 2, 3 or 4 substituents selected from OH, halogen, $C_1$-$C_6$ alkyl or $C_1$-$C_6$ alkoxy;
comprising at least one reaction step, in which carbon dioxide and hydrogen are reacted with at least one compound of the general formulae (II.a) or (II.b)

wherein
$R^1$ is as defined above;
$R^2$ is a divalent group selected from linear $C_2$-$C_9$ alkanediyl, wherein the alkanediyl is unsubstituted or substituted by 1, 2, 3 or 4 substituents selected from OH, halogen, $C_1$-$C_6$ alkyl or $C_1$-$C_6$ alkoxy;
in the presence of
at least one transition metal catalyst complex, comprising at least one polydentate ligand containing at least three phosphorus atoms which are capable of coordinating to the transition metal, wherein the transition metal is selected from metals of groups 7, 8, 9 and 10 of the periodic table of the elements according to IUPAC;
at least one monodentate ligand containing one phosphorus atom;
at least one Lewis acid.

The invention also relates to a mixture comprising the least one polydentate ligand and at least one monodentate ligand.

The invention also relates to the use of the mixtures comprising the least one polydentate ligand and at least one monodentate ligand in transition metal complexes for the preparation of acetals.

DETAILED DESCRIPTION OF THE INVENTION

In the sense of the invention the term "monodentate ligand" is a compound which has only one donor atom or donor atom group.

In the sense of the invention the term "polydentate ligand" is a compound which can simultaneously form a coordinative bond with the transition metal atom via at least three donor atoms or donor atom groups.

In the sense of the invention the term "turn over number (TON)" is the number of moles of the substrate that a mol of catalyst can convert before becoming inactivated.

The terms "reaction mixture" and "reaction medium" are used synonymously. In the sense of the invention these terms are referred to a mixture comprising compound (II.a) or (II.b), Lewis acid, at least one a transition metal catalyst complex, and at least one monodentate ligand.

In the sense of the invention, the expression "alkyl" means straight-chain and branched alkyl groups. Preferred are straight-chain or branched $C_1$-$C_{20}$-alkyl groups, more preferably $C_1$-$C_{12}$-alkyl groups, even more preferably $C_1$-$C_8$-alkyl groups and in particular $C_1$-$C_6$-alkyl groups. Examples of alkyl groups are particularly methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl and decyl.

The expression "alkyl" also comprises substituted alkyl groups, which may carry 1, 2, 3, 4 or 5 substituents, preferably 1, 2 or 3 substituents and particularly preferably 1 substituent, selected from the groups of cycloalkyl, heterocycloalkyl, aryl, hetaryl, alkoxy, cycloalkoxy, heterocycloalkoxy, aryloxy, hetaryloxy, hydroxyl, mercapto, polyalkylene oxide, polyalkyleneimine, P(aryl)$_2$, halogen, nitro, formyl, acyl and cyano, NE$^1$E$^2$, NE$^1$E$^2$E$^{3+}$X$^-$, COOH, carboxylate, SO$_3$H and sulfonate, wherein E$^1$, E$^2$ and E$^3$ and X$^-$ are defined below.

The term "haloalkyl" refers to a straight-chain or branched alkyl group as defined above, where some or all of the hydrogen atoms in these groups may be replaced by halogen atoms as mentioned above. A preferred fluorinated alkyl group is trifluoromethyl. The expression "alkyl" also comprises alkyl groups which are interrupted by one or more non-adjacent oxygen atoms, preferably alkoxyalkyl.

The expression "alkylene" in the sense of the present invention stands for straight or branched alkanediyl groups with preferably 1 to 6 carbon atoms. These are methylene (—CH$_2$—), ethylene (—CH$_2$—CH$_2$—), n-propylene (trimethylene) (—CH$_2$—CH$_2$—CH$_2$—), isopropylene (—CH$_2$—CH(CH$_3$)—), tetramethylene (—CH$_2$—CH$_2$—CH$_2$—CH$_2$—), pentamethylene (—CH$_2$—CH$_2$—CH$_2$—CH$_2$—CH$_2$—) and hexamethylene (—CH$_2$—CH$_2$—CH$_2$—CH$_2$—CH$_2$—CH$_2$—) etc.

The expression "alkanetriyl" in the sense of the present invention stands for straight-chain or branched alkanetriyl groups with preferably 1 to 10 carbon atoms. These are C—(CH$_2$)$_n$H, C—(CH$_2$)$_n$—CH$_3$, wherein n is from 0 to 8.

The expression "cycloalkyl" in the sense of the present invention comprises unsubstituted and substituted cycloalkyl groups, preferably C$_5$-C$_7$-cycloalkyl groups such as cyclopentyl, cyclohexyl or cycloheptyl, which, if substituted, may carry 1, 2, 3, 4 or 5 substituents, preferably 1, 2 or 3 substituents and particularly preferred 1 substituent selected from the groups alkyl, alkoxy, halogen heterocycloalkyl, aryl, hetaryl, cycloalkoxy, heterocycloalkoxy, aryloxy, hetaryloxy, hydroxyl, mercapto, polyalkylene oxide, polyalkyleneimine, P(aryl)$_2$, nitro, formyl, acyl and cyano, NE$^1$E$^2$, NE$^1$E$^2$E$^{3+}$X$^-$, COOH, carboxylate, SO$_3$H and sulfonate, wherein E$^1$, E$^2$, E$^3$ and X$^-$ are defined below.

The expression "heterocycloalkyl" in the sense of the present invention comprises saturated or partially unsaturated cycloaliphatic groups with preferably 3 to 7, more preferably 4 to 7, especially 5 or 6 ring atoms, in which 1, 2, 3 or 4 ring atoms may be replaced with heteroatoms, preferably selected from the elements oxygen, nitrogen and sulfur and which are optionally substituted. If substituted, these heterocycloaliphatic groups carry preferably 1, 2 or 3 substituents, more preferably 1 or 2 substituents and in particular 1 substituent. These substituents are preferably selected from alkyl, cycloalkyl, aryl, COOR (R=H, alkyl, cycloalkyl, aryl), COO$^-$M$^+$ and NE$^1$E$^2$, more preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

In the context of the present invention, the expression "aryl" includes mono- or polycyclic aromatic hydrocarbon radicals typically having 6 to 10 carbon atoms. Examples of aryl are especially phenyl, naphthyl, fluorenyl, anthracenyl, phenanthrenyl and naphthacenyl, preferably phenyl and naphthyl.

Substituted aryls may have one or more substituents (e.g. 1, 2, 3, 4 or 5) depending on the number and size of their ring systems. These are each preferably independently selected from alkyl, alkoxy, carboxyl, carboxylate, trifluoromethyl, —SO$_3$H, sulfonate, NE$^1$E$^2$, alkylene-NE$^1$E$^2$, nitro, cyano and halogen. Examples of substituted aryl radicals are tolyl, xylyl, mesityl. A preferred fluorinated aryl group is pentafluorophenyl.

The expression "hetaryl" also denotes as "heteroaryl", which is synonymously used, in the sense of the present invention comprises unsubstituted or substituted heterocycloaromatic groups, preferably pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl, and carbazolyl; in case these heterocycloaromatic groups are substituted they may carry preferably 1, 2 or 3 substituents selected from the groups alkyl, alkoxy, carboxyl, carboxylate, —SO$_3$H, sulfonate, NE$^1$E$^2$, alkylene-NE$^1$E$^2$, trifluoromethyl, and halogen. A preferred substituted indolyl group is 3-methylindolyl.

In the sense of the present invention the terms "carboxylate" and "sulfonate" preferably stand for a derivative of a carboxylic acid function or a sulfonic acid function, in particular a metal carboxylate or metal sulfonate, a carboxylic acid ester or sulfonic acid ester or a carboxylic acid amide or sulfonic acid amide. Particularly preferred are esters with C$_1$-C$_4$-alkanols like methanol, ethanol, n-propanol, isopropanol, n-butanol, sec-butanol and tert-butanol. Preferred are also the primary amides and their N-alkyl and N,N-dialkyl derivatives.

In the sense of the present invention the term "alkoxy" is a alkyl group, as defined above, attached via an oxygen atom. C$_1$-C$_2$-Alkoxy is methoxy or ethoxy. C$_1$-C$_4$-Alkoxy is, for example, methoxy, ethoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-Alkoxy includes the meanings given for $C_1$-$C_4$-alkoxy and also includes, for example, pentoxy, 1-methylbutoxy, 2-methylbutoxy, 3-methylbutoxy, 1,1-dimethylpropoxy, 1,2-dimethylpropoxy, 2,2-dimethyl propoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. "Alkoxy" may carry 1, 2, 3, 4 or 5 substituents, preferably 1, 2 or 3 substituents and particularly preferably 1 substituent, selected from halogen.

The term "haloalkyloxy" is a haloalkyl group, as defined above, attached via an oxygen atom.

The term "cycloalkoxy" refers to a cycalkyl group as defined above attached via an oxygen atom.

The term "aryloxy" refers to an aryl group as defined above attached via an oxygen atom.

The term "heterocycloalkoxy" refers to a heterocycloalkyl group as defined above attached via an oxygen atom.

The term "hetaryloxy" refers to a hetaryl group as defined above attached via an oxygen atom.

The term "cycloolefine" refers to cycloalkanes, which are defined as monocyclic hydrocarbon radicals with at least one C—C double bond in the ring, which ring is however not aromatic. Preferably, the hydrocarbon radicals have 3 to 8 carbon atoms ($C_3$-$C_8$-cycloalkene).

The term "olefine" refers to alkenylene, which are linear or branched ethylenically mono unsaturated hydrocarbon groups having 2 to 20, e.g. 2 to 10 or 2 to 6 carbon atoms and a C=C-double bond in any position.

The term "diene" refers to an olefine that contains two double bonds.

In the sense of the present invention the expression "acyl" stands for alkanoyl groups or aroyl groups with preferably 2 to 11, more preferably 2 to 8 carbon atoms, for example acetyl, propanoyl, butanoyl, pentanoyl, hexanoyl, heptanoyl, 2-ethylhexanoyl, 2-propylheptanoyl, benzoyl and naphthoyl.

The groups $NE^1E^2$, $NE^4E^5$ are preferably selected from N,N-dimethylamino, N,N-diethylamino, N,N-dipropylamino, N,N-di isopropylamino, N,N-di-n-butylamino, N,N-di-tert-butylamino, N,N-dicyclohexylamino and N,N-diphenylamino.

Halogen stands for fluorine, chlorine, bromine or iodine, preferably fluorine, chlorine or bromine.

$M^+$ stands for a cation equivalent, which means a monovalent cation or the part of a polyvalent cation representing a positive single charge. The cation $M^+$ is only a counter ion which neutralizes negatively charged substituents like the $COO^-$ or the sulfonate group and which can principally be selected arbitrarily. Preferred are alkaline metal ions, in particular $Na^+$, $K^+$ and $Li^+$ ions, or onium ions like ammonium ions, mono-, di-, tri-, tetraalkylammonium ions, phosphonium ions, tetraalkylphosphonium ions and tetraarylphosphonium ions.

The same applies to the anion equivalent $X^-$ which is only a counter ion for positively charged substituents such as the ammonium group and which can principally be selected arbitrarily among monovalent anions and the parts of polyvalent anions which correspond to a single negative charge. Preferred are halogenides $X^-$, in particular chloride and bromide. Also preferred are sulfates and sulfonates, in particular $SO_4^{2-}$, tosylate, trifluoromethane sulfonate and methyl sulfonate.

Condensed ring systems are aromatic, heteroaromatic or cyclic compounds which have fused-on rings obtained via anellation. Condensed ring systems consist of two, three or more than three rings. Depending on the type of connection, one distinguishes between ortho-anellation and peri-anellation. In case of ortho-anellation each ring has two atoms in common with each adjacent ring. In case of peri-anellation a carbon atom belongs to more than two rings. Preferred among the condensed ring systems are ortho-condensed ring systems.

Starting Materials and Reaction Conditions

In order to obtain compounds of formula (I) at least one alcohol compound of formula (II.a) or (II.b),

wherein $R^1$ and $R^2$ have the meaning as defined above, is used as starting material.

Preferably, $R^1$ is selected from $C_1$-$C_{20}$ alkyl, which is unsubstituted or substituted with 1, 2, 3, 4 or 5 substituents selected from OH, halogen, $C_1$-$C_6$ alkoxy or $C_6$-$C_{10}$ aryl, more preferably $C_1$-$C_6$ alkyl which is unsubstituted or substituted with 1, 2, 3 or 4 substituents selected from OH, halogen, $C_1$-$C_4$ alkoxy, especially $C_1$-$C_4$ alkyl, which is unsubstituted or substituted with 1 or 2 selected from OH or halogen, in particular $C_1$-$C_4$ alkyl which is unsubstituted, especially $C_1$-$C_2$ alkyl.

In a special embodiment $R^1$ is methyl.

Preferably, $R^2$ is selected from linear $C_2$-$C_6$-alkanediyl, wherein the alkanediyl is unsubstituted or substituted by 1, 2 or 3 substituents selected from OH, halogen, $C_1$-$C_4$ alkyl or $C_1$-$C_4$ alkoxy, more preferably $C_2$-$C_5$-alkanediyl, wherein the alkanediyl is unsubstituted or substituted by 1 or 2 substituents selected from $C_1$-$C_2$ alkyl, especially $C_2$-$C_5$-alkanediyl, wherein the alkanediyl is unsubstituted or substituted by 1 substituted substituent selected from $C_1$-$C_2$ alkyl.

In a special embodiment $R^2$ is —$CH_2$—$CH_2$—, —$CH_2$—$CH_2$—$CH_2$—, —$CH_2$—$CH_2$—$CH(CH_3)$—, —$CH_2$—$CH(CH_3)$—$CH_2$— or —$CH_2$—$CH(CH_3)$—.

The hydrogen ($H_2$) used for the reduction reaction can be used in pure form or, if desired, also in the form of mixtures with at least one other gas, preferably inert gases, such as nitrogen or argon. Preference is given to using $H_2$ in undiluted form.

The reaction is typically carried at an $H_2$ pressure in the range from 0.1 to 400 bar, preferably in the range from 5 to 200 bar, more preferably in the range from 10 to 180 bar.

The carbon dioxide ($CO_2$) used for the reaction can be used in pure form or, if desired, also in the form of mixtures with at least one other gas, preferably inert gases, such as nitrogen or argon. Preference is given to using $CO_2$ in undiluted form. The $CO_2$ can be used in its gaseous form, liquefied or in the supercritical state.

The reaction is typically carried at a $CO_2$ pressure in the range from 0.1 to 400 bar, preferably in the range from 5 to 200 bar, more preferably in the range from 10 to 70 bar.

The ratio between $H_2$ and $CO_2$ can be varied and is preferably in a range between 1:100 to 100:1, more preferably between 1:30 to 30:1 and most preferably between 1:10 and 10:1.

The reaction can principally be performed continuously, semi-continuously or discontinuously. Preference is given to a continuous process.

The reaction can principally be performed in all reactors known to a person skilled in the art for catalyzed gas-liquid reaction who will, therefore, select the reactors accordingly. Suitable reactors are described for example, in Ullmanns Enzyklopädie der technischen Chemie, vol. 1, 3rd edition, 1951, p. 743 ff. or in Ullmanns Enzyklopädie der technischen Chemie, vol. 1, 3rd edition, 1951, p. 769 ff. Preferably, an autoclave is employed for the reaction which may have an internal stirrer and an internal lining.

The process according to the invention can be performed in a wide temperature range. Preferably, the reaction is performed at a temperature in the range from 20° C. to 200° C., more preferably in the range from 50° C. to 180° C., in particular in the range from 60° C. to 170° C.

The process according to the invention can be performed in a wide pressure range. Preferably, the reaction is performed at a pressure in the range from 1 to 400 bar, more preferably in the range from 10 to 300 bar, in particular in the range from 40 to 200 bar.

The reaction can also be run in combination with an inert solvent in addition to the alcohol compound of formula (II.a) or (II.b). Suitable solvents are selected from aliphatic hydrocarbons, aromatic hydrocarbons, esters, ethers and mixtures thereof.

The process of the invention can be carried out without or with a further solvent. In one preferred embodiment the reaction is carried out in the presence of a further solvent. In another preferred embodiment the reaction is carried out without a further solvent.

Suitable solvents are selected from aliphatic hydrocarbons, aromatic hydrocarbons, amides, esters, ethers, and mixtures thereof. Preferred solvents are
- aliphatic hydrocarbons such as pentane, hexane, heptane, octane or cyclohexane;
- aromatic hydrocarbons such as benzene, toluene, xylenes, ethylbenzene, mesitylene or benzotrifluoride;
- esters such as methyl acetate, ethyl acetate, t-butyl acetate;
- ethers such as dioxane, tetrahydrofuran, diethyl ether, dibutyl ether, methyl butyl ether, diisopropyl ether or diethylene glycol dimethyl ether.

If desired, mixtures of two or more of the aforementioned solvents can also be used.

Preference is given to using aliphatic hydrocarbons, aromatic hydrocarbons and mixtures thereof as solvents.

The molar ratio of the compound of formula (II.a) or (II.b) to the additional solvent used is preferably in the range between 50:1 to 1:50, more preferably between 2:1 to 1:30, in particular 2:1 to 1:10.

A Lewis acid is a chemical species that contains an empty orbital which is capable of accepting an electron pair from a Lewis base to form a Lewis acid base adduct.

Suitable Lewis acids are $AlCl_3$, $ZnCl_2$, $PF_5$, $AsCl_3$, $SnCl_4$, $TiCl_4$, $SbCl_5$, $Al(OTf)_3$, $Sc(OTf)_3$, $Fe(OTf)_3$, $Yb(OTf)_3$, $Eu(OTf)_3$, $B(C_6F_5)_3$, $B(2,4-(CF_3)_2C_6H_3)_3$, $BF_3$, $BF_3*Et_2O$, $BF_3*THF$, $Ag(OTf)$, $Pr(OTf)_3 Zn(OTf)_3$ and mixtures thereof, in particular $Al(OTf)_3$, $Sc(OTf)_3$, $Fe(OTf)_3$, $Yb(OTf)_3$, $Eu(OTf)_3$, $B(C_6F_5)_3$, $B(2,4-(CF_3)_2C_6H_3)_3$, $BF_3$, $BF_3*Et_2O$, $BF_3*THF$, $Ag(OTf)$, $Pr(OTf)_3 Zn(OTf)_3$, and mixtures thereof.

In a preferred embodiment $Al(OTf)_3$ is used as Lewis acid.

The amount of the Lewis acid is preferably from 1 to 1000 mol %, especially from 50 to 500 mol %, based on the used transition metal catalyst.

Catalyst

In the process of the invention, the production of compound (I) is performed in a liquid reaction medium in the presence of a transition metal catalyst complex. According to the invention, a homogeneous transition metal catalyst complex is used. That means the transition metal catalyst complex is dissolved in the liquid reaction medium under the reaction condition. In other words, the transition metal catalyst complex is in the same phase as the reactants.

The transition metal of the transition metal catalyst complex is selected from metals of groups 7, 8, 9 and 10 of the periodic table of the elements according to IUPAC. In a preferred embodiment the metal of the transition metal catalyst complex is selected from ruthenium, iron, osminum, cobalt, rhodium, rhenium, iridium, nickel, platinum and palladium, in particular ruthenium and nickel, especially ruthenium and cobalt.

In a preferred embodiment, the ligand is selected from organo-phosphines, organo-phosphites, organo-phosphonites, organo-phosphinites, and organo-phosphoramidites.

Organo-phosphines are derived from phosphines (also called phosphanes), wherein one or more hydrogens are replaced by an organic substituent.

Organo-phosphites are esters of phosphonic acid $P(OH)_3$, having the general structure $P(OR)_3$, wherein R is an organic substituent.

Organo-phosphonites are esters of the phosphonous acid $HP(OH)_2$, having the general structure $P(OR)_2R'$, wherein R and R' are the same or different organic substituents.

Organo-phosphinites are esters of the phosphinous acid $H_2P(OH)$, having the general structure $(P(OR)R'_2)$, wherein R and R' are the same or different organic substituents.

Organo-phosphoramidites are formally derived from organo phosphites, wherein at least one OR radical substituent is replaced by amid radical $NR_2$, wherein R is hydrogen or an organic substituents.

In a preferred embodiment of the invention, the at least one polydentate ligand is selected from compounds of formula (III)

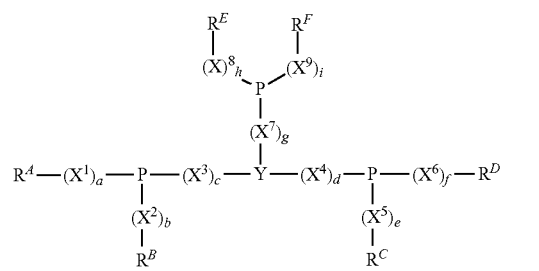

wherein
$R^A$, $R^B$, $R^C$, $R^D$, $R^E$ and $R^F$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, $P(aryl)_2$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl, and aryl, and $X^-$ is an anion equivalent, and wherein the radicals cycloalkyl, heterocycloalkyl, aryl and hetaryl $R^A$, $R^B$, $R^C$, $R^D$, $R^E$ and $R^F$ may carry 1, 2, 3, 4 or 5 substituents selected from alkyl and the substituents mentioned for the alkyl radicals $R^A$, $R^B$, $R^C$, $R^D$, $R^E$ and $R^F$ before, or $R^A$ and $R^B$ and/or $R^C$ and $R^D$ and/or $R^E$ and $R^F$ together with the P atom and, if present, the groups $X^1$, $X^2$, $X^5$, $X^6$, $X^8$ and $X^9$ to which they are bound, are a 5- to 8-membered heterocycle which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, formyl, acyl and cyano, wherein $E^4$, $E^5$ and $E^6$ are the same or different and are selected from hydrogen, alkyl, cycloalkyl and aryl and $X^-$ is an anion equivalent, $X^1$, $X^2$, $X^5$, $X^6$, $X^8$ and $X^9$ are independently from each other O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, $X^3$, $X^4$ and $X^7$ are independently from each other $C_1$-$C_{10}$ alkanediyl, O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is a bridging group, selected from $C_1$-$C_{10}$ alkanetriyl, N or P a, b, c, d, e, f, g, h and i are independently from each other 0 or 1.

In another preferred embodiment of the invention, the transition metal catalyst complex comprises at least one polydentate ligand, selected from compounds of formula (III), wherein $R^A$, $R^B$, $R^C$, $R^D$, $R^E$ and $R^F$ are independently from each other $C_1$-$C_{10}$ alkyl, $C_3$-$C_{10}$ cycloalkyl, $C_6$-$C_{10}$ aryl, heterocycloalkyl, or hetaryl, wherein $C_1$-$C_{10}$ alkyl is unsubstituted or carries 1, 2, 3, 4 or 5 substituents selected from F, Cl, Br, OH, CN, $NH_2$, $C_6$-$C_{10}$ aryl or P(aryl)$_2$, wherein aryl and the aryl moiety of P(aryl)$_2$ in the two last-mentioned radicals is unsubstituted or substituted with $C_1$-$C_{10}$ alkyl, $C_1$-$C_{10}$-haloalkyl, $C_1$-$C_{10}$ alkoxy or $C_1$-$C_{10}$ haloalkoxy;

wherein $C_3$-$C_{10}$-cycloalkyl is unsubstituted or carries 1, 2, 3, 4 or 5 substituents selected from halogen, OH, CN, $NH_2$, $C_1$-$C_{10}$ alkyl, $C_6$-$C_{10}$ aryl or P(aryl)$_2$, wherein aryl and the aryl moiety of P(aryl)$_2$ in the two last-mentioned radicals is unsubstituted or substituted with 1, 2, 3, 4 or 5 $C_1$-$C_{10}$ alkyl, $C_1$-$C_{10}$-haloalkyl, $C_1$-$C_{10}$ alkoxy or $C_1$-$C_{10}$ haloalkoxy;

wherein $C_6$-$C_{10}$ aryl is unsubstituted or carries 1, 2, 3, 4 or 5 substituents selected from OH, $C_1$-$C_{10}$ alkyl, $C_1$-$C_{10}$ haloalkyl, $C_1$-$C_{10}$-alkoxy, $C_1$-$C_{10}$ haloalkoxy or $C_6$-$C_{10}$ aryl which is unsubstituted or substituted by OH;

wherein heterocycloalkyl is a 3-, 4-, 5-, 6-, 7- or 8-membered saturated or partly saturated heteromonocyclic ring containing one, two or three heteroatoms selected from O, S or N as ring members or a 7-, 8-, 9-, 10-, 11- or 12-membered saturated or partly saturated heterobicyclic ring containing one, two, three or four heteroatoms selected from O, S or N as ring members; where the heteromonocyclic ring and the heterobicyclic ring may carry 1, 2, 3, 4 or 5 substituents selected from halogen, OH, CN, $NH_2$, or $C_1$-$C_{10}$ alkyl;

wherein hetaryl is a 5- or 6-membered monocyclic heteroaromatic ring containing 1, 2, 3 or 4 heteroatoms selected from the group consisting of N, O and S as ring members, and a 9- or 10-membered bicyclic heteroaromatic ring containing 1, 2, 3 or 4 heteroatoms selected from the group consisting of N, O and S as ring members, where the monocyclic or bicyclic heteroaromatic ring may carry 1, 2, 3, 4 or 5 substituents selected from halogen, OH, CN, $NH_2$ or $C_1$-$C_{10}$ alkyl; or $R^A$ and $R^B$ and/or $R^C$ and $R^D$ and/or $R^E$ and $R^F$ together with the P atom and, if present, the groups $X^1$, $X^2$, $X^5$ and $X^6$, $X^8$ and $X^9$ to which they are bound, are a 5- to 8-membered heterocycle which is optionally fused with one, two or three groups selected from $C_5$-$C_{10}$ cycloalkyl, $C_6$-$C_{10}$ aryl, 5- or 6-membered monocyclic heteroaromatic ring containing 1, 2, 3 or 4 heteroatoms selected from the group consisting of N, O and S as ring members, or 9- or 10-membered bicyclic heteroaromatic ring containing 1, 2, 3 or 4 heteroatoms selected from the group consisting of N, O and S as ring members heteroaryl, wherein the heterocycle and, if present, the fused-on groups independently from each other may each carry 1, 2, 3 or 4 substituents selected from $C_1$-$C_{10}$-alkyl, $X^1$, $X^2$, $X^5$, $X^6$, $X^8$ and $X^9$ are independently from each other O, S, $SiR^xR^y$ or $NR^z$, wherein $R^x$, $R^y$ and $R^z$ are independently from each other hydrogen, $C_1$-$C_{10}$ alkyl, $C_3$-$C_{10}$ cycloalkyl, heterocycloalkyl, $C_6$-$C_{10}$ aryl or hetaryl, $X^3$, $X^4$ and $X^7$ are independently from each other $C_1$-$C_{10}$ alkanediyl, O, S, $SiR^xR^y$ or $NR^z$, wherein $R^x$, $R^y$ and $R^z$ are independently from each other hydrogen, $C_1$-$C_{10}$ alkyl, $C_3$-$C_{10}$ cycloalkyl or $C_6$-$C_{10}$ aryl;

Y is a bridging group, selected from $C_1$-$C_{10}$ alkanetriyl, N or P, a, b, c, d, e, f, g, h, i, are independently from each other 0 or 1.

In another preferred embodiment of the invention, the at least one transition metal catalyst comprises at least one polydentate ligand selected from compounds of formula (III), wherein $R^A$, $R^B$, $R^C$, $R^D$, $R^E$ and $R^F$ are independently from each other alkyl, aryl or heteroaryl, wherein the alkyl, aryl or heteroaryl radicals may carry 1, 2, 3, 4 or 5 substituents selected from alkoxy, $NE^1E^2$, $NE^1E^2E^{3+}X^-$, wherein $E^1$, $E^2$ and $E^3$ are the same or different and are selected from hydrogen or alkyl and $X^-$ is an anion equivalent, $X^1$, $X^2$, $X^5$, $X^6$, $X^8$ and $X^9$ are independently from each other O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is a bridging group, selected from $C_1$-$C_6$-alkanetriyl or N, $X^3$, $X^4$, $X^7$ are methylene, ethylene, trimethylene, tetramethylene, pentamethylene and hexamethylene;

a, b, e, f, h and i are independently from each other 0 or 1, preferably 0, c, d and g are 0 or 1, preferably 1.

In another preferred embodiment of the invention, the transition metal catalyst complex comprises at least one polydentate ligand selected from compounds of formula (III), wherein $R^A$, $R^B$, $R^C$, $R^D$, $R^E$ and $R^F$ are independently from each other $C_1$-$C_{10}$ alkyl, $C_3$-$C_{10}$ cycloalkyl, $C_6$-$C_{10}$ aryl, heterocycloalkyl, or hetaryl, wherein $C_1$-$C_{10}$ alkyl is unsubstituted or carries 1, 2, 3, 4 or 5 substituents selected from F, Cl, Br, OH, CN, $NH_2$, $C_6$-$C_{10}$ aryl or P(aryl)$_2$, wherein aryl and the aryl moiety of P(aryl)$_2$ in the two last-mentioned radicals is unsubstituted or substituted with $C_1$-$C_{10}$ alkyl, $C_1$-$C_{10}$-haloalkyl, $C_1$-$C_{10}$ alkoxy or $C_1$-$C_{10}$ haloalkoxy;

wherein $C_3$-$C_{10}$-cycloalkyl is unsubstituted or carries 1, 2, 3, 4 or 5 substituents selected from halogen, OH, CN, NH$_2$, $C_1$-$C_{10}$ alkyl, $C_6$-$C_{10}$ aryl or P(aryl)$_2$, wherein aryl and the aryl moiety of P(aryl)$_2$ in the two last-mentioned radicals is unsubstituted or substituted with 1, 2, 3, 4 or 5 $C_1$-$C_{10}$ alkyl, $C_1$-$C_{10}$-haloalkyl, $C_1$-$C_{10}$ alkoxy or $C_1$-$C_{10}$ haloalkoxy;

wherein $C_6$-$C_{10}$ aryl is unsubstituted or carries 1, 2, 3, 4 or 5 substituents selected from OH, $C_1$-$C_{10}$ alkyl, $C_1$-$C_{10}$ haloalkyl, $C_1$-$C_{10}$-alkoxy, $C_1$-$C_{10}$ haloalkoxy or $C_6$-$C_{10}$ aryl which is unsubstituted or substituted by OH;

wherein heterocycloalkyl is a 3-, 4-, 5-, 6-, 7- or 8-membered saturated or partly saturated heteromonocyclic ring containing one, two or three heteroatoms selected from O, S or N as ring members or a 7-, 8-, 9-, 10-, 11- or 12-membered saturated or partly saturated heterobicyclic ring containing one, two, three or four heteroatoms selected from O, S or N as ring members; where the heteromonocyclic ring and the heterobicyclic ring may carry 1, 2, 3, 4 or 5 substituents selected from halogen, OH, CN, NH$_2$, or $C_1$-$C_{10}$ alkyl;

wherein hetaryl is a 5- or 6-membered monocyclic heteroaromatic ring containing 1, 2, 3 or 4 heteroatoms selected from the group consisting of N, O and S as ring members, and a 9- or 10-membered bicyclic heteroaromatic ring containing 1, 2, 3 or 4 heteroatoms selected from the group consisting of N, O and S as ring members, where the monocyclic or bicyclic heteroaromatic ring may carry 1, 2, 3, 4 or 5 substituents selected from halogen, OH, CN, NH$_2$ or $C_1$-$C_{10}$ alkyl; or $R^A$ and $R^B$ and/or $R^C$ and $R^D$ and/or $R^E$ and $R^F$ together with the P atom and, if present, the groups $X^1$, $X^2$, $X^5$ and $X^6$, $X^8$ and $X^9$ to which they are bound, are a 5- to 8-membered heterocycle which is optionally fused with one, two or three groups selected from $C_5$-$C_{10}$ cycloalkyl, $C_6$-$C_{10}$ aryl, 5- or 6-membered monocyclic heteroaromatic ring containing 1, 2, 3 or 4 heteroatoms selected from the group consisting of N, O and S as ring members, or 9- or 10-membered bicyclic heteroaromatic ring containing 1, 2, 3 or 4 heteroatoms selected from the group consisting of N, O and S as ring members heteroaryl, wherein the heterocycle and, if present, the fused-on groups independently from each other may each carry 1, 2, 3 or 4 substituents selected from $C_1$-$C_{10}$-alkyl, $X^1$, $X^2$, $X^6$, $X^6$, $X^8$ and $X^9$ are independently from each other O, S, SiR$^x$R$^y$ or NR$^z$, wherein R$^x$, R$^y$ and R$^z$ are independently from each other hydrogen, $C_1$-$C_{10}$ alkyl, $C_3$-$C_{10}$ cycloalkyl, heterocycloalkyl, $C_6$-$C_{10}$ aryl or hetaryl, $X^3$, $X^4$ and $X^7$ are independently from each other $C_1$-$C_{10}$ alkanediyl, O, S, SiR$^x$R$^y$ or NR$^z$, wherein R$^x$, R$^y$ and R$^z$ are independently from each other hydrogen, $C_1$-$C_{10}$ alkyl, $C_3$-$C_{10}$ cycloalkyl or $C_6$-$C_{10}$ aryl;

Y is a bridging group, selected from $C_1$-$C_{10}$ alkanetriyl, N or P, a, b, c, d, e, f, g, h, i, are independently from each other 0 or 1.

Preferably, Y is, irrespectively of its occurrence, is a bridging group selected from $C_1$-$C_{10}$ alkanetriyl, N or P, more preferably $C_1$-$C_6$ alkanetriyl or N, especially $C_1$-$C_2$ alkanetriyl or N.

Preferably, $X^3$, $X^4$ and $X^7$ are irrespectively of their occurrence, preferably independently from each other $C_1$-$C_{10}$ alkanediyl, O, S, SiR$^x$R$^y$ or NR$^z$, wherein R$^x$, R$^y$ and R$^z$ are independently from each other hydrogen, alkyl, cycloalkyl, heterocycloalkyl, aryl or hetaryl, more preferably $C_1$-$C_{10}$ alkanediyl, especially methylene, ethylene, trimethylene, tetramethylene, pentamethylene and hexamethylene.

A particularly preferred group of embodiment relates to polydentate ligands of formula (III.a),

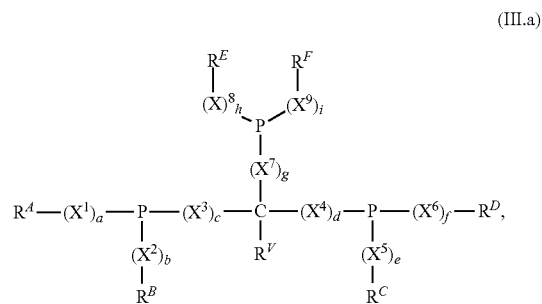

(III.a)

wherein $R^A$, $R^B$, $R^C$, $R^D$, $R^E$ and $R^F$ have one of the meanings as defined above. In particular $R^A$, $R^B$, $R^C$, $R^D$, $R^E$ and $R^F$ are independently selected from $C_6$-$C_{10}$ aryl, which is unsubstituted or carries 1, 2, 3 or 4 substituents selected from OH, $C_1$-$C_6$ alkyl, $C_1$-$C_6$ haloalkyl, $C_1$-$C_6$-alkoxy or $C_1$-$C_6$ haloalkoxy. Especially $R^A$, $R^B$, $R^C$, $R^D$, $R^E$ and $R^F$ are phenyl.

a, b, e, f, h and i are independently from each other 0 or 1. Preferably a, b, e, f, h and i are 0.

c, d and g are 0 or 1. Preferably, c, d and g are 1.

$X^3$, $X^4$ and $X^7$ are independently selected from each other $C_1$-$C_{10}$ alkanediyl. Especially $X^3$, $X^4$ and $X^7$ are selected from methylene, ethylene, trimethylene, tetramethylene, pentamethylene and hexamethylene. In particular $X^3$, $X^4$ and $X^7$ are selected from methylene, ethylene.

$R^V$ is selected from hydrogen or $C_1$-$C_6$ alkyl. Especially, $R^V$ is selected from methyl, ethyl, propyl, isopropyl. In particular, RV is methyl.

Another particularly preferred group of embodiment relates to polydentate ligands of formula (III.b),

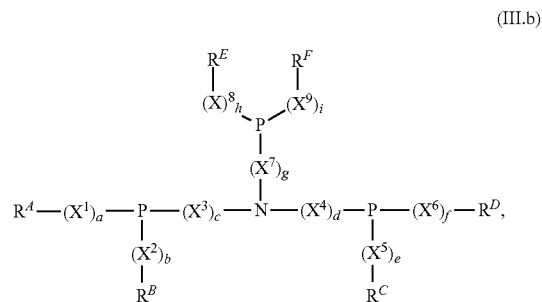

(III.b)

wherein $R^A$, $R^B$, $R^C$, $R^D$, $R^E$ and $R^F$ have one of the meanings as defined above. In particular $R^A$, $R^B$, $R^C$, $R^D$, $R^E$ and $R^F$ are independently selected from $C_6$-$C_{10}$ aryl, which is unsubstituted or carries 1, 2, 3 or 4 substituents selected from OH, $C_1$-$C_6$ alkyl, $C_1$-$C_6$ haloalkyl, $C_1$-$C_6$-alkoxy or $C_1$-$C_6$ haloalkoxy. Especially $R^A$, $R^B$, $R^C$, $R^D$, $R^E$ and $R^F$ are phenyl.

a, b, e, f, h and i are independently from each other 0 or 1. Preferably a, b, e, f, h and i are 0.

c, d and g are 0 or 1. Preferably, c, d and g are 1.

$X^3$, $X^4$ and $X^7$ are independently selected from each other $C_1$-$C_{10}$ alkanediyl. Especially $X^3$, $X^4$ and $X^7$ are selected from methylene, ethylene, trimethylene, tetramethylene, pentamethylene and hexamethylene. In particular $X^3$, $X^4$ and $X^7$ are selected from methylene, ethylene.

Another particularly preferred group of embodiment relates to polydentate ligands of formula (III.c),

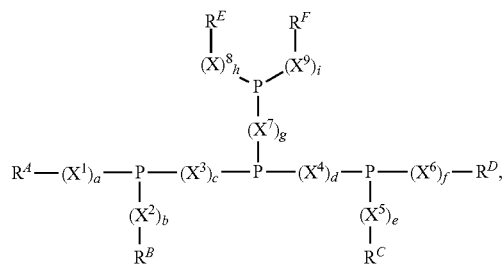

(III.c)

wherein $R^A$, $R^B$, $R^C$, $R^D$, $R^E$ and $R^F$ have one of the meanings as defined above. In particular $R^A$, $R^B$, $R^C$, $R^D$, $R^E$ and $R^F$ are independently selected from $C_6$-$C_{10}$ aryl, which is unsubstituted or carries 1, 2, 3 or 4 substituents selected from OH, $C_1$-$C_6$ alkyl, $C_1$-$C_6$ haloalkyl, $C_1$-$C_6$-alkoxy or $C_1$-$C_6$ haloalkoxy. Especially $R^A$, $R^B$, $R^C$, $R^D$, $R^E$ and $R^F$ are phenyl.

a, b, e, f, h and i are independently from each other 0 or 1. Preferably a, b, e, f, h and i are 0.

c, d and g are 0 or 1. Preferably, c, d and g are 1.

$X^3$, $X^4$ and $X^7$ are independently selected from each other $C_1$-$C_{10}$ alkanediyl. Especially $X^3$, $X^4$ and $X^7$ are selected from methylene, ethylene, trimethylene, tetramethylene, pentamethylene and hexamethylene. In particular $X^3$, $X^4$ and $X^7$ are selected from methylene, ethylene.

Further the liquid reaction medium can comprise at least one further ligand, which is different from the polydentate ligand and the monodentate ligand. In this embodiment the transition metal catalyst complex of the inventive process comprises at least one further ligand selected from hydrido, halides, amides, carboxylates, acetylacetonate, aryl- or alkylsufonates, CO, olefins, dienes, cycloolefines, nitriles, aromatics, and heteroaromatics.

In a preferred embodiment the transition metal catalyst complex is selected from Ru(tris(diphenylphosphinomethyl)ethane)(2-methylallyl)], [Ru(tris(diphenylphosphinomethyl)ethane)(H)$_2$], [Ru(tris(diphenylphosphinomethypamine)(2-methylallyl)], [Ru(tris(diphenylphosphinomethyl)amine)(H)$_2$], [Ru(tris(diphenylphosphinoethyl)amine)(2-methylallyl)] or [Ru(tris(diphenylphosphinoethyl)amine)(H)$_2$].

The transition metal catalyst according to the invention can be employed in the form of a preformed metal complex which comprises the metal compound and one or more ligands. Alternatively, the transition metal catalyst is formed in situ in the reaction medium by combining a metal compound, herein also termed pre-catalyst, with one or more suitable ligands to form a catalytically active metal complex in the reaction medium. It is also possible that the transition metal catalyst is formed in situ in the presence of an auxiliary ligand by combining a metal compound, herein also termed pre-catalyst, with one or more auxiliary ligands to form a catalytically active metal complex in the reaction medium.

Suitable pre-catalysts are selected from neutral metal complexes, oxides and salts of metals of groups 7, 8, 9 and 10 of the periodic table of the elements. Preferred pre-catalysts are selected from metal complexes, oxides and salts of ruthenium, rhenium, iridium, nickel, platinum or palladium.

Ruthenium compounds that are useful as pre-catalyst are, for example, [Ru(methylallyl)$_2$COD], [Ru(p-cymene)Cl$_2$]$_2$, [Ru(benzene)Cl$_2$]$_n$, [Ru(CO)$_2$Cl$_2$]$_n$, [Ru(CO)$_3$Cl$_2$]$_2$, [Ru(COD)(allyl)], [RuCl$_3$.H$_2$O], [Ru(acetylacetonate)$_3$], [Ru(DMSO)$_4$Cl$_2$], [Ru(PPh$_3$)$_3$(CO)(H)Cl], [Ru(PPh$_3$)$_3$(CO)Cl$_2$], [Ru(PPh$_3$)$_3$(CO)(H)$_2$], [Ru(PPh$_3$)$_3$Cl$_2$], [Ru(Cp)(PPh$_3$)$_2$ Cl], [Ru(Cp) (CO)$_2$Cl], [Ru(Cp)(CO)$_2$H], [Ru(Cp)(CO)$_2$]$_2$, [Ru(Cp*)(CO)$_2$Cl], [Ru(Cp*)(CO)$_2$H], [Ru(Cp*)(CO)$_2$]$_2$, [Ru(indenyl)(CO)$_2$Cl], [Ru(indenyl)(CO)$_2$H], [Ru(indenyl)(CO)$_2$]$_2$, ruthenocen, [Ru(binap)(Cl)$_2$], [Ru(2,2'-bipyridin)$_2$(Cl)$_2$.H$_2$O], [Ru(COD)(Cl)$_2$H]$_2$, [Ru(Cp*)(COD)Cl], [Ru$_3$(CO)$_{12}$], [Ru(tetraphenyl-hydroxycyclopentadienyl)(CO)$_2$H], [Ru(PMe$_3$)$_4$(H)$_2$], [Ru(PEt$_3$)$_4$(H)$_2$], [Ru(Pn-Pr$_3$)$_4$(H)$_2$], [Ru(Pn-Bu$_3$)$_4$(H)$_2$], [Ru(Pn-octyl$_3$)$_4$(H)$_2$], of which [Ru(methylallyl)$_2$COD], Ru(COD)Cl$_2$]$_2$, [Ru(Pn-Bu$_3$)$_4$(H)$_2$], [Ru(Pn-octyl$_3$)$_4$(H)$_2$], [Ru(PPh$_3$)$_3$ (CO)(H)Cl] and [Ru(PPh$_3$)$_3$(CO)(H)$_2$] are preferred, in particular [Ru(methylallyl)$_2$COD].

Iridium compounds that are useful as pre-catalyst are, for example, [IrCl$_3$.H$_2$O], KIrCl$_4$, K$_3$IrCl$_6$, [Ir(COD)Cl]$_2$, [Ir(cyclooctene)$_2$Cl]$_2$, [Ir(ethene)$_2$Cl]$_2$, [Ir(Cp)Cl$_2$]$_2$, [Ir(Cp*)Cl$_2$]$_2$, [Ir(Cp)(CO)$_2$], [Ir(Cp*)(CO)$_2$], [Ir(PPh$_3$)$_2$(CO)Cl] and [Ir(PPh$_3$)$_3$Cl], of which [Ir(COD)Cl]$_2$, [Ir(cyclooctene)$_2$Cl]$_2$ and [Ir(Cp*)Cl$_2$]$_2$ are preferred.

Nickel compounds that are useful as pre-catalyst are, for example [Ni(COD)$_2$], Ni(CO)$_4$, NiCl$_2$, NiBr$_2$, NiI$_2$, Ni(OAc)$_2$[Ni(AcAc)$_2$], [Ni(Cl)$_2$(TMEDA)], [Ni(Cl)$_2$(DME)], [Ni(Br)$_2$(DME)], [Ni(Cl)$_2$(PPh$_3$)$_2$], [Ni(CO)$_2$(PPh$_3$)], [Ni(Cl)(methallyl)]$_2$, [Ni(CO$_3$)], nickel(II)diemthylglyoxime, nickel(II)2-ethylhexanoate, nickel(II) hexafluroacetlyacetonate, bis(N,N'-di-t-butylacetamidinato)nickel(II), nickel(II)oxalate, Ni(NO$_3$)$_2$, nickel(II)stearate, Ni(SO$_4$), nickel(II)tetrafluoroborate hexahydrate, nickel(II)trifluoroaceylacetonate dehydrate, nickel(II)trifluoromethanesulfonate.

Rhenium compounds that are useful as pre-catalyst are, for example ammoniumperrhenate, chlorotricarbonyl(2,2'-bipyridine)rhenium(I), chlorotricarbonyl(4,4'-di-t-butyl-2,2'-bipyridine)rhenium(I), cyclopentadienylrhenium tricarbonyl, iododioxobis(triphenylphosphine)rhenium(V), methyltrioxorhenium(VII), pentamethylcyclopentadienylrhenium tricarbonyl, rhenium carbonyl, rhenium(V) chloride, rhenium pentacarbonyl bromide, trifluoromethylsulfonatotricarbonyl(2,2'-bipyridine)rhenium(I).

Platinum compounds that are useful as pre-catalyst are, for example ammonium tetrachloroplatinate(II), bis(tri-t-butylphosphine)platinum (0), bis(ethylenediamine)platinum (II) chloride, dibromo(1,5-cyclooctadiene)platinum(II), dichlorobis(benzonitrile)platinum(II), cis-dichlorobis(diethylsulfide)platinum(II), cis-dichlorobis(pyridine)platinum (II), cis-dichlorobis(triethylphosphine)platinum(II), dichloro(1,5-cyclooctadiene)platinum(II), cis-dichlorodiamine platinum(II), di-μ-chloro-dichlorobis(ethylene)diplatinum(II), dichloro(dicyclopentadienyl)platinum(II), di-μ-iodo-bis(ethylenediamine)diplatinum(I I) nitrate, diiodo(1,5-cyclooctadiene)platinum(II), dimethyl(1,5-cyclooctadiene)platinum(II), platinum(II) acetylacetonate, platinum(II) acetylacetonate, platinum(II) bromide, platinum(II) chloride, platinum(II) iodide, potassium bis(oxalato)platinate(II) dihydrate, tetrakis(triphenylphosphine)platinum(0), tris(dibenzylideneacetone)diplatinum(0).

Palladium compounds that are useful as pre-catalyst are, for example allyl(cyclopentadienyl)palladium(II), bis[(trimethylsilyl)methyl](1,5-cyclooctadiene)-palladium(II), allylpalladium chloride dimer, ammonium tetrachloropalladate(II), bis[1,2-bis(diphenylphosphino)ethane]palladium(0), bis(dibenzylideneacetone)palladium(0), trans-bis(dicyclohexylamine)bis(acetato)-palladium(II), bis(2-methylallyl) palladium chloride dimer, bis(tri-t-butylphosphine)-palladium(0), bis(tricyclohexylphosphine)palladium(0), bis(tri-o-tolylphosphine)-palladium(0), chloromethyl(1,5-cyclooctadiene)palladium(II), diacetato[1,3-bis(diphenyl-phosphino)propane]palladium(II), diacetatobis(triphenylphosphine)palladium(II), diacetato(1,10-phenanthroline)palladium(II), di-p-bromobis(tri-t-butylphosphino)-dipalladium(I), trans-dibromobis(triphenylphosphine)palladium(II), dibromo(1,5-cyclooctadiene)palladium(II), dichlorobis(benzonitrile)palladium(II), dichlorobis(di-t-butylphenylphosphino)palladium(I I), di-p-chlorobis{2-[(dimethylamino)methyl]-phenyl}dipalladium, trans-dichlorobis(tricyclohexylphosphine)palladium(II), trans-dichlorobis(triphenylphosphine)palladium(II), dichloro(1,5-cyclooctadiene)-palladium(II), dichloro(norbornadiene)palladium(II), cis-dichloro(N,N,N',N'-tetramethylethylenediamine)palladium(II), cis-dimethyl(N,N,N',N'-tetramethylethylenediamine)-palladium(II), (1-methylallyl)palladium chloride dimer, palladium(II) acetate, palladium (II) acetylacetonate, palladium(II) benzoate, palladium(II) bromide, palladium(II) chloride, palladium(II) hexafluoroacetylacetonate, palladium(II) iodide, palladium(II) sulfate, palladium(II) trifluoroacetate, palladium(II) trimethylacetate, tetrakis(triphenylphosphine)palladium(0), tris(dibenzylideneacetone)dipalladium(0).

In the aforementioned compound names "COD" denotes 1,5-cyclooctadiene; "Cp" denotes cyclopentadienyl; "Cp*" denotes pentamethylcyopentadienyl; and "binap" denotes 2,2'-bis(diphenylphosphino)-1,1'-binaphthyl.

In the process of the invention, a substoichiometric amount of catalyst is generally used, with the amount of catalyst typically not exceeding 50 mol %, frequently not exceeding 20 mol % and in particular not exceeding 10 mol % or not exceeding 5 mol %, based on the amount of compound (II). An amount of catalyst of from 0.001 to 50 mol %, frequently from 0.001 mol % to 20 mol % and in particular from 0.005 to 5 mol %, based on the amount of compound (II), is generally used in the process of the invention. Preference is given to using an amount of catalyst from 0.01 to 2 mol % and particularly preferably from 0.01 mol % to 1 mol %. All amounts of catalyst indicated are calculated as transition metal and based on the amount of compound (II).

Monodentate Ligand

In the process of the invention, the production of compound (I) is performed in a liquid reaction medium in the presence of a transition metal catalyst complex and at least one monodentate ligand containing one phosphorus atom.

In a preferred embodiment, the monodentate ligand is selected from organo-phosphines, organo-phosphites, organo-phosphonites, organo-phosphinites and organo-phosphoramidites. These P containing compounds are defined above.

In a preferred embodiment of the invention, the at least one monodentate ligand selected from compounds of formula (IV)

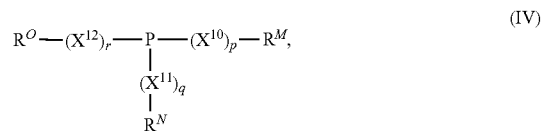

$R^M$, $R^N$ and $R^O$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl, and aryl and $X^-$ is an anion equivalent, and wherein the radicals cycloalkyl, heterocycloalkyl, aryl and hetaryl $R^M$, $R^N$ and $R^O$ may carry 1, 2, 3, 4 or 5 substituents selected from alkyl and the substituents mentioned for the alkyl radicals $R^G$, $R^H$ and $R^I$ before, or $R^M$ and $R^N$ or $R^N$ and $R^O$ together with the P atom and, if present, the groups $X^{10}$, $X^{11}$ and $X^{12}$ to which they are bound, are a 5- to 8-membered heterocycle which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, formyl, acyl and cyano, wherein $E^4$, $E^5$ and $E^6$ are the same or different and are selected from hydrogen, alkyl, cycloalkyl and aryl and $X^-$ is an anion equivalent, $X^{10}$, $X^{11}$ and $X^{12}$ are independently from each other O, S, $CR^xR^y$, $SiR^xR^y$ or $NR^z$, wherein $R^x$, $R^y$ and $R^z$ are independently from each other hydrogen, alkyl, cycloalkyl, heterocycloalkyl, aryl or hetaryl, p, q and r are independently from each other 0 or 1.

In another preferred embodiment of the invention, the at least one monodentate ligand is selected from compounds of formula (IV), wherein $R^M$, $R^N$ and $R^O$ are independently from each other $C_1$-$C_{10}$ alkyl, $C_3$-$C_{10}$ cycloalkyl, $C_6$-$C_{10}$ aryl, heterocycloalkyl, or hetaryl, wherein $C_1$-$C_{10}$ alkyl is unsubstituted or carries 1, 2, 3, 4 or 5 substituents selected from F, Cl, Br, OH, CN, $NH_2$, $C_6$-$C_{10}$ aryl or P(aryl)$_2$, wherein aryl and the aryl moiety of P(aryl)$_2$ in the two last-mentioned radicals is unsubstituted or substituted with $C_1$-$C_{10}$ alkyl, $C_1$-$C_{10}$-haloalkyl, $C_1$-$C_{10}$ alkoxy or $C_1$-$C_{10}$ haloalkoxy;

wherein $C_3$-$C_{10}$-cycloalkyl is unsubstituted or carries 1, 2, 3, 4 or 5 substituents selected from halogen, OH, CN, $NH_2$, $C_1$-$C_{10}$ alkyl, $C_6$-$C_{10}$ aryl or P(aryl)$_2$, wherein aryl and the aryl moiety of P(aryl)$_2$ in the two last-mentioned radicals is unsubstituted or substituted with 1, 2, 3, 4 or 5 $C_1$-$C_{10}$ alkyl, $C_1$-$C_{10}$-haloalkyl, $C_1$-$C_{10}$ alkoxy or $C_1$-$C_{10}$ haloalkoxy;

wherein $C_6$-$C_{10}$ aryl is unsubstituted or carries 1, 2, 3, 4 or 5 substituents selected from OH, $C_1$-$C_{10}$ alkyl, $C_1$-$C_{10}$ haloalkyl, $C_1$-$C_{10}$-alkoxy, $C_1$-$C_{10}$ haloalkoxy or $C_6$-$C_{10}$ aryl which is unsubstituted or substituted by OH;

wherein heterocycloalkyl is a 3-, 4-, 5-, 6-, 7- or 8-membered saturated or partly saturated heteromonocyclic ring containing one, two or three heteroatoms selected from O, S or N as ring members or a 7-, 8-, 9-, 10-, 11- or 12-membered saturated or partly saturated heterobicyclic ring containing one, two, three or four heteroatoms selected from O, S or N as ring members; where the heteromonocyclic ring and the heterobicyclic ring may carry 1, 2, 3, 4 or 5 substituents selected from halogen, OH, CN, $NH_2$, or $C_1$-$C_{10}$ alkyl;

wherein hetaryl is a 5- or 6-membered monocyclic heteroaromatic ring containing 1, 2, 3 or 4 heteroatoms selected from the group consisting of N, O and S as ring members, and a 9- or 10-membered bicyclic heteroaromatic ring containing 1, 2, 3 or 4 heteroatoms selected from the group consisting of N, O and S as ring members, where the monocyclic or bicyclic heteroaromatic ring may carry 1, 2, 3, 4 or 5 substituents selected from halogen, OH, CN, $NH_2$ or $C_1$-$C_{10}$ alkyl;

or $R^M$ and $R^N$ or $R^N$ and $R^O$ together with the P atom and, if present, the groups $X^{10}$, $X^{11}$, or the groups $X^{11}$ and $X^{12}$ to which they are bound, are a 5- to 8-membered heterocycle which is optionally fused with one, two or three groups selected from $C_5$-$C_{10}$ cycloalkyl, $C_6$-$C_{10}$ aryl, 5- or 6-membered monocyclic heteroaromatic ring containing 1, 2, 3 or 4 heteroatoms selected from the group consisting of N, O and S as ring members, or 9- or 10-membered bicyclic heteroaromatic ring containing 1, 2, 3 or 4 heteroatoms selected from the group consisting of N, O and S as ring members heteroaryl, wherein the heterocycle and, if present, the fused-on groups independently from each other may each carry 1, 2, 3 or 4 substituents selected from $C_1$-$C_{10}$-alkyl, $X^{10}$, $X^{11}$ and $X^{12}$ are independently from each other O, S, $SiR^xR^y$ or $NR^z$, wherein $R^x$, $R^y$ and $R^z$ are independently from each other hydrogen, $C_1$-$C_{10}$ alkyl, $C_3$-$C_{10}$ cycloalkyl or $C_6$-$C_{10}$ aryl, p, q and r are independently from each other 0 or 1.

In a particular preferred embodiment of the invention, the at least one monodentate ligand is selected from compounds of formula (IV), wherein $R^M$, $R^N$ and $R^O$ are independently from each other $C_1$-$C_6$ alkyl or $C_6$-$C_{10}$ aryl, in $C_1$-$C_6$ alkyl or $C_6$-$C_{10}$ particular $C_1$-$C_4$ alkyl, phenyl, wherein $C_1$-$C_6$ alkyl is unsubstituted or carries 1, 2, 3, 4 or 5 substituents selected from F, Cl, Br, OH, CN, $NH_2$;

wherein $C_6$-$C_{10}$ aryl is unsubstituted or carries 1, 2, 3, 4 or 5 substituents selected from OH, $C_1$-$C_4$ alkyl, $C_1$-$C_4$ haloalkyl, $C_1$-$C_4$-alkoxy, $C_1$-$C_4$ haloalkoxy, in particular methyl, ethyl, $CF_3$, methoxy, ethoxy;

$X^{10}$, $X^{11}$ and $X^{12}$ are independently from each other O, S, p, q and r are independently from each other 0 or 1.

In a special embodiment the least one monodentate ligand is selected from triphenylphosphine, tris(p-tolyl)phosphine, tris(4-methoxyphenyl)phosphine, tris(4-trifluoromethylphenyl)phosphine, tris(o-tolyl)phosphine, triphenylphosphite and trimethylphosphite.

In the process of the invention, the at least one monodentate ligand is generally used in excess based on the amount of transition metal catalyst complex.

Preferably the molar ratio of the transition metal catalyst complex to the at least one monodentate ligand is in the range of 1:5.0 to 1:1.1, more preferably in the range of 1:3.0 to 1:1.2, particularly in the range of 1:2.5 to 1:1.3.

In a preferred embodiment the at least one polydentate ligand is selected from tris(diphenylphosphinomethyl)methane or tris(diphenylphosphinomethyl)amine and the at least one monodentate ligand is selected from triphenylphosphite.

According to the process of the invention a compound (I)

(I)

is obtained, wherein $R^1$ has one of the meanings as defined above.

Preferably, $R^1$ is selected from $C_1$-$C_{20}$ alkyl, which is unsubstituted or substituted with 1, 2, 3, 4 or 5 substituents selected from OH, halogen, $C_1$-$C_6$ alkoxy or $C_6$-$C_{10}$ aryl, more preferably $C_1$-$C_6$ alkyl which is unsubstituted or substituted with 1, 2, 3 or 4 substituents selected from OH, halogen, $C_1$-$C_4$ alkoxy, especially $C_1$-$C_4$ alkyl, which is unsubstituted or substituted with 1 or 2 selected from OH or halogen, in particular $C_1$-$C_4$ alkyl which is unsubstituted, especially $C_1$-$C_2$ alkyl.

In one embodiment both $R^1$ have the same meaning.

In a special embodiment $R^1$ is methyl.

In another preferred embodiment both $R^1$ form together a divalent bridging group $R^2$; which is preferably selected from linear $C_2$-$C_6$-alkanediyl, wherein the alkanediyl is unsubstituted or substituted by 1, 2 or 3 substituents selected from OH, halogen, $C_1$-$C_4$ alkyl or $C_1$-$C_4$ alkoxy, more preferably $C_2$-$C_5$-alkanediyl, wherein the alkanediyl is unsubstituted or substituted by 1 or 2 substituents selected from $C_1$-$C_2$ alkyl, especially $C_2$-$C_5$-alkanediyl, wherein the alkanediyl is unsubstituted or substituted by 1 substituted substituents selected from $C_1$-$C_2$ alkyl.

In a special embodiment $R^2$ is —$CH_2$—$CH_2$—, —$CH_2$—$CH_2$—$CH_2$—, —$CH_2$—$CH_2$—$CH(CH_3)$—, —$CH_2$—$CH$($CH_3$)—$CH_2$— or —$CH_2$—$CH(CH_3)$—.

Generally, a composition comprising the compound of the formula (I), the catalyst, monodentate ligand, water, Lewis acid and unreacted alcohol of formula (II.a) or (II.b) is obtained. The work-up of the reaction mixture of the inventive process and the isolation of the acetals are carried out in a customary manner, for example by filtration, an extractive work-up or by a distillation, for example under reduced pressure. The compound of the formula (I) may be obtained in sufficient purity by applying such measures or a combination thereof, obviating additional purification steps. Alternatively, further purification can be accomplished by methods commonly used in the art, such as such as chromatography In one embodiment of the present invention, the inventive process is characterized in that the compound of the formula (I) is separated from the transition metal catalyst via distillation.

The distillation residue usually still comprises the transition metal catalyst, the Lewis acid and the monodentate ligand in an active form, which can be reused in a new reaction to prepare a compound of formula (I), in a new process cycle. As long as the distillation conditions, in particular the temperature treatment, are not too harsh, the transition metal catalyst remains active.

In one embodiment of the present invention, the inventive process is characterized in that the homogeneous transition metal catalyst is recycled by removing the compound of the formula (I) and other volatile compounds of the reaction mixture via distillation.

A further aspect of the invention relates to a mixture comprising the least one polydentate ligand and at least one monodentate ligand as defined above.

In a preferred embodiment the mixture comprises at least one polydentate ligand selected from tris(diphenylphosphinomethyl)ethane or tris(diphenylphosphinomethyl)amine and at least one monodentate ligand selected from triphenylphosphine, tris(p-tolyl)phosphine, tris(4-methoxyphenyl)phosphine, tris(4-trifluoromethylphenyl)phosphine, tris(o-tolyl)phosphine, triphenylphosphite and trimethylphosphite.

In another preferred embodiment the mixture comprises at least one polydentate ligand and at least one monodentate ligand as defined above, wherein the molar ratio of the transition metal catalyst complex to the least one monodentate ligand is in the range of is in the range of 1:5.0 to 1:1.1, more preferably in the range of 1:3.0 to 1:1.2, particularly in the range of 1:2.5 to 1:1.3.

A further aspect of the invention relates to the use of the mixtures comprising the least one polydentate ligand and at least one monodentate ligand in transition metal complexes for the preparation of compounds (I) as defined above.

The invention is described in more detail in the following examples.

EXAMPLES

All chemicals and solvents were purchased from Sigma-Aldrich, Merck or ABCR and were used without further purification.

The following abbreviations are used:
MF: Methyl formate
DMM: Dimethoxymethane
Triphos: 1,1,1-tris(diphenylphosphinomethyl)ethane
COD: 1,5-cyclooctadiene
Ph: Phenyl
Tol: Tolyl General:

Chemicals were purchased from commercial suppliers and used as delivered. 1,1,1-Tris(diphenylphosphinomethyl)ethane (triphos), Ru(PPh$_3$)$_4$H$_2$, and bis(2-methyl-allyl)(1,5-cyclooctadiene)ruthenium(II) were purchased from Merck. Ru(triphos)(tmm) was synthesized according to the previous report (*Chem Cat Chem* 2013, 5, 439-441). Dry solvents were dispensed from the solvent purification system MB SPS-800. Reactions requiring inert conditions were carried out in flame-dried glassware under an atmosphere of nitrogen using standard Schlenk-techniques. NMR spectra were, if not mentioned otherwise, recorded at room temperature on the following spectrometers: Bruker Avance-III-300, Bruker Avance DRX-300, Bruker-Avance DRX-500 and Bruker Avance-III-500. Chemical shifts were given in ppm and coupling constants in Hz. $^1$H and $^{13}$C spectra were calibrated in relation to deuterated solvents, namely CDCl$_3$ (7.26 ppm; 77.16 ppm).

Example 1

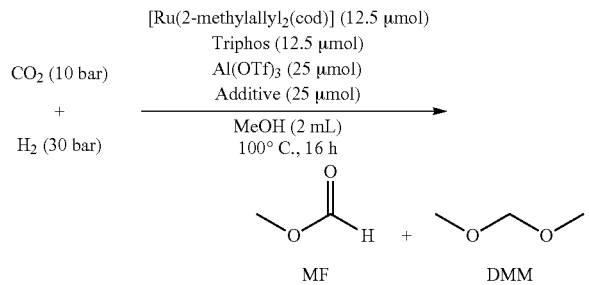

In an argon filled glovebox, ruthenium precursor (12.5 μmol), triphos ligand (12.5 μmol), Al(OTf)$_3$ (25 μmol), additive (25 μmol) and MeOH (2 mL) were added to a vial fitted with a magnetic stirrer bar and sealed. The vial was placed in a high pressure Paar reactor steel autoclave (inner volume 300 mL). The autoclave was tightly closed and purged with CO$_2$ twice. The reactor was opened and the two microwave vial seals were perforated with wide bore needles to allow gas transfer, and the autoclave was sealed and purged with CO$_2$ and finally pressurized with CO$_2$ (10 bar) and H$_2$ (30 bar) to a pressure of 40 bar (total pressure). A heating ring was used to bring the autoclave to the desired temperature (100° C.), and was stirred at 600 rpm for 16 h. The autoclave was cooled to room temperature with ice bath then vented. Mesitylene was added to the vial as an internal standard, and then the resulting solution was transferred to NMR tube in CDCl$_3$ and analyzed by $^1$H NMR. The experimental data are shown in table 1.

TABLE 1

| Experiment | monodentate Ligand (additive) | TON of MF | TON of DMM |
|---|---|---|---|
| 1 (comparative) | none | 18 | 4 |
| 2 | Ph$_3$P | 21 | 32 |
| 3 | p-Tol$_3$P | 21 | 32 |
| 4 | (4-MeOC$_6$H$_4$)$_3$P | 21 | 29 |
| 5 | (PhO)$_3$P | 18 | 46 |
| 6$^a$ | (PhO)$_3$P | 24 | 46 |

$^a$Using [Ru(triphos)(tmm)] (12.5 μmol) instead of [Ru(2-methylallyl)$_2$(COD)] (12.5 μmol) and triphos (12.5 μmol)

At a pressure of 40 bar the positive effect of different phosphines with regard to activity and selectivity towards DMM can clearly be shown. The data demonstrate that the examples according to the invention show a significant higher TON towards DMM than in the comparative experiment 1.

Example 2

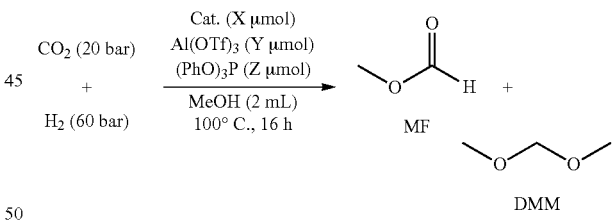

In an argon filled glovebox, ruthenium precursor (12.5 μmol), triphos ligand (12.5 μmol) if necessary, Al(OTf)$_3$ (Y, 25 μmol), additive (Z, 25 μmol) and MeOH (2 mL) were added to a vial fitted with a magnetic stirrer bar and sealed. The vial was placed in a high pressure Paar reactor steel autoclave (inner volume 300 mL). The autoclave was tightly closed and purged with CO$_2$ twice. The reactor was opened and the two microwave vial seals were perforated with wide bore needles to allow gas transfer, and the autoclave was sealed and purged with CO$_2$ and finally pressurized with CO$_2$ (20 bar) and H$_2$ (60 bar) to the a pressure of 80 bar (total pressure). A heating ring was used to bring the autoclave to the desired temperature (100° C.), and was stirred at 600 rpm for 16 h. The autoclave was cooled to room temperature with ice bath then vented. Mesitylene was added to the vial as an internal standard, and then the resulting solution was transferred to NMR tube in CDCl₃ and analyzed by ¹H NMR. The experimental date are shown in table 2.

TABLE 2

| Experiment | Cat[a] | X | Y | Z | TON of MF | TON of DMM |
|---|---|---|---|---|---|---|
| 7 (comparative) | A | 12.5 | 25 | 0 | 48 | 83 |
| 8 | A | 12.5 | 25 | 25 | 44 | 95 |
| 9 | B | 12.5 | 25 | 25 | 49 | 92 |
| 10 | A | 6.0 | 12 | 12 | 71 | 148 |
| 11 | B | 6.0 | 12 | 12 | 54 | 114 |
| 12 | C | 6.0 | 12 | 0 | 70 | 160 |

[a]A: [Ru(triphos)(tmm)]
B: [Ru(2-methylallyl)₂(COD)] and triphos
C: Ru(PPh₃)₄H₂ and triphos At the pressure of 80 bar, the activity could further be increased up to a TON$_{DMM}$ of 160 in the presences of P(Ph)₃ as monodentate ligand (see exp. 12) (compared to ex. 2, table 1). In the comparative experiment 7 the achieved TON$_{DMM}$ of 83 is significantly lower.

Example 3

Screening tests were carried out in 8 parallel steel autoclave reactors (inner volume 300 mL). The general experimental procedure for each screening experiment was as follows: in a first step, a starting reaction mixture was prepared by filling 79.2 g (100 mL) of solvent (MeOH), 90 mg (125 µmol) of Ru-catalyst (Ru(triphos)(tmm)), 237.095 mg (500 µmol) of Al(OTf)₃, and 155.14 (500 µmol) of monodentate ligand P(OPh)₃, into a steel autoclave reactor (inner volume 300 mL). In a second step, the filled steel autoclave reactor was tightly sealed and pressurized with 100 bar H₂ and 20 bar CO₂ (total pressure of 120 bar) and the steel autoclave reactor was heated to a temperature of 100° C. while stirring at 2000 rpm. After the corresponding reaction temperature was reached, the reaction temperature was maintained for given reaction time, while continuing stirring the reaction mixture inside the heated and pressurized steel autoclave reactor. Subsequently, the steel autoclave reactor was allowed to cool down to room temperature (approximately 22° C.), the pressure was released and the steel autoclave reactor was opened. For further analysis, 1 mL of the resulting reaction mixture was subjected to GC analysis to quantify said reaction products.

GC Method: Column: Varian CP7475 CP-Sil 5 CB; 60 m*320 µm*8 µm, Injection volume: 1 µL, Inlet: 250° C., Split: 20:1, Flow: 5 mL/min constant flow, Oven: start temp. 40° C. hold for 3 minutes, 20° C./min to 225° C. hold for 8.25 min. The experimental data are shown in table 3.

TABLE 3

| Experiment | Time [h] | TON of MF | TON of DMM |
|---|---|---|---|
| 13 | 8 | 191 | 857 |
| 14 | 10 | 170 | 890 |
| 15 | 12 | 166 | 930 |
| 16 | 14 | 171 | 962 |
| 17 | 16 | 160 | 913 |
| 18 | 36 | 141 | 780 |

A further increase in activity and selectivity is achieved by combining Ru(triphos)(tmm) and P(OPh)₃ (125 µmol of Ru-catalysts in 100 mL of MeOH) and high-pressure CO₂ (20 bar) and H₂ (100 bar) using steel autoclaves. A reaction time screening indicated the highest TON$_{DMM}$ (=962) was achieved after 14 h (see example 16). Ru(triphos)(tmm) without P(OPh)₃ under the same conditions gave ~700 turnover numbers at most. The increasing rate of TON$_{DMM}$ (~40%) as well as a significant reduction of the MF-formation showed the positive effect of monodentate ligand P(OPh)₃.

Example 4

The mixture obtained in experiment 16 was subjected a rotary evaporator, until all the solvent and liquid products were evaporated under air. The remaining solid was transferred to a glove box and added into a still autoclave reactor (inner volume 300 mL), together with 79.2 g (100 mL) of solvent (MeOH). In a second step, the filled steel autoclave reactor was tightly sealed and pressurized with 100 bar H₂ and 20 bar CO₂ (total pressure of 120 bar) and the steel autoclave reactor was heated to a temperature of 100° C. while stirring at 2000 rpm. After the corresponding reaction temperature was reached, the reaction temperature was maintained for 12 h while continuing stirring the reaction mixture inside the heated and pressurized steel autoclave reactor. Subsequently, the steel autoclave reactor was allowed to cool down to room temperature (approximately 22° C.), the pressure was released and the steel autoclave reactor was opened. For further analysis, 1 mL of the resulting reaction mixture was subjected to GC analysis to quantify said reaction products.

GC Method: Column: Varian CP7475 CP-Sil 5 CB; 60 m*320 µm*8 µm, Injection volume: 1 µL, Inlet: 250° C., Split: 20:1, Flow: 5 mL/min constant flow, Oven: start temp. 40° C. hold for 3 minutes, 20° C./min to 225° C. hold for 8.25 min. The experimental data are shown in table 4.

TABLE 4

| Experiment 19 | TON of MF | TON of DMM |
|---|---|---|
| first run | 171 | 962 |
| second run | 161 | 709 |

The reuse of Ru-catalysts with the following method is also demonstrated, which means according to experiment 19 a catalyst's activity recovery of 74%.

What is claimed is:
1. A process for the production of a compound of the formula (I)

(I)

wherein
each R¹ is independently from each other selected from C₁-C₄₀ alkyl, which is unsubstituted or substituted with 1, 2, 3, 4 or 5 substituents selected from OH, halogen, C₁-C₆ alkoxy or C₆-C₂₀ aryl;
or both R¹ form together a divalent bridging group R² selected from linear C₂-C₉-alkanediyl, wherein the alkanediyl is unsubstituted or substituted by 1, 2, 3 or 4 substituents selected from OH, halogen, C₁-C₆ alkyl or C₁-C₆ alkoxy;
the process comprising at least one reaction step, in which carbon dioxide and hydrogen are reacted with at least one compound of the general formulae (II.a) or (II.b)

 (II.a),

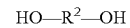 (II.b), wherein

R¹ is as defined above;

R² is a divalent group selected from linear $C_2$-$C_9$ alkanediyl, wherein the alkanediyl is unsubstituted or substituted by 1, 2, 3 or 4 substituents selected from OH, halogen, $C_1$-$C_6$ alkyl or $C_1$-$C_6$ alkoxy;

in the presence of at least one transition metal catalyst complex, comprising at least one polydentate ligand containing at least three phosphorus atoms which are capable of coordinating to the transition metal, wherein the transition metal is selected from metals of groups 7, 8, 9 and 10 of the periodic table of the elements according to IUPAC; and at least one monodentate ligand containing one phosphorus atom; and at least one Lewis acid.

2. The process according to claim 1, wherein the molar ratio of the transition metal catalyst complex to the at least one monodentate ligand is in the range of 1:5.0 to 1:1.1.

3. The process according to claim 1, wherein the metal of the transition metal catalyst complex is selected from ruthenium, iron, osmium, cobalt, rhodium, rhenium, iridium, nickel, platinum and palladium.

4. The process according to claim 3, wherein the metal of the transition metal catalyst complex is ruthenium or cobalt.

5. The process according to claim 1, wherein the polydentate ligand is selected from organo-phosphines, organo-phosphites, organo-phosphonites, organo-phosphinites and organo-phosphoramidites.

6. The process according to claim 5, wherein the transition metal catalyst complex comprises at least one polydentate ligand of formula (III)

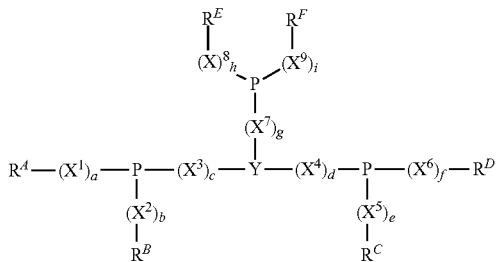

(III)

wherein $R^A$, $R^B$, $R^C$, $R^D$, $R^E$ and $R^F$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $P(aryl)_2$, $SO_3H$, sulfonate, $NE^1E^2$, $NE^1E^2E^{3+}X^-$, halogen, nitro, formyl, acyl and cyano, wherein E1, E2 and E3 are the same or different and are selected from hydrogen, alkyl, cycloalkyl, and aryl and X is an anion equivalent, and wherein the radicals cycloalkyl, heterocycloalkyl, aryl and hetaryl $R^A$, $R^B$, $R^C$, $R^D$, $R^E$ and $R^F$ may carry 1, 2, 3, 4 or 5 substituents selected from alkyl and the substituents mentioned for the alkyl radicals $R^A$, $R^B$, $R^C$, $R^D$, $R^E$ and $R^F$ before, or $R^A$ and $R^B$ and/or $R^C$ and $R^D$ and/or $R^E$ and $R^F$ together with the P atom and, if present, the groups $X^1$, $X^2$, $X^5$, $X^6$, $X^8$ and $X^9$ to which they are bound, are a 5-to 8-membered heterocycle which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^6X^-$, nitro, alkoxycarbonyl, formyl, acyl and cyano, wherein $E^4$, $E^5$ and $E^6$ are the same or different and are selected from hydrogen, alkyl, cycloalkyl and aryl and X is an anion equivalent, $X^1$, $X^2$, $X^5$, $X^6$, $X^8$ and $X^9$ are independently from each other O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, $X^3$, $X^4$ and $X^7$ are independently from each other $C_1$-$C_{10}$ alkanediyl, O, S, $SiR^xR^y$ or $NR^z$, wherein $R^x$, $R^y$ and $R^z$ are independently from each other hydrogen, alkyl, cycloalkyl, heterocycloalkyl, aryl or hetaryl, Y is a bridging group, comprising $C_1$-$C_{10}$ alkanetriyl, N or P, a, b, c, d, e, f, g, h and i are independently from each other 0 or 1.

7. The process according to claim 6, wherein the transition metal catalyst complex comprises at least one ligand of formula (III), wherein $R^A$, $R^B$, $R^C$, $R^D$, $R^E$ and $R^F$ are independently from each other alkyl, aryl or heteroaryl, wherein the alkyl, aryl or heteroaryl radicals may carry 1, 2, 3, 4 or 5 substituents selected from alkoxy, $NE^1E^2$, $NE^1E^2E^{3+}X^-$, wherein $E^1$, $E^2$ and $E^3$ are the same or different and are selected from hydrogen or alkyl and $X^-$ is an anion equivalent, $X^1$, $X^2$, $X^5$, $X^6$, $X^8$ and $X^9$ are as defined in claim 6, $X^3$, $X^4$ and $X^7$ are methylene, ethylene, trimethylene, tetramethylene, pentamethylene and hexamethylene, Y is a bridging group, selected from $C_1$-$C_6$-alkanetriyl or N, and a, b, e, f, h and i are independently from each other 0 or 1.

8. The process according to claim 7, wherein a, b, e, f, h, and i are 0, and c, d, and g are 1.

9. The process according to claim 1, wherein the transition metal catalyst complex comprises at least one further ligand selected from the group consisting hydrido, halides, amides, carboxylates, acetylacetonate, aryl- or alkylsufonates, CO, olefins, dienes, cycloolefines, nitriles, aromatics and heteroaromatics.

10. The process according to claim 1, where the transition metal catalyst complex is selected from the group consisting of [Ru(tris(diphenylphosphinomethyl)ethane)(2-methylallyl)], [Ru(tris(diphenylphosphinomethyl)ethane)(H)$_2$], [Ru(tris(diphenylphosphinomethyl)amine)(2-methylallyl)], [Ru(tris(diphenylphosphinomethyl)amine)(H)$_2$], [Ru(tris(diphenylphosphinoethyl)amine)(2-methylallyl)] and [Ru(tris(diphenylphosphinoethyl)amine)(H)$_2$].

11. The process according to claim 1, wherein an amount of the transition metal catalyst complex is 50 mol % or less calculated as transition metal and based on the amount of compound (II.a) or (II.b) used.

12. The process according to claim 11, wherein an amount of the transition metal catalyst complex at the most of 20 mol %, calculated as transition metal and based on the amount of compound (II.a) or (II.b), is used.

13. The process according to claim 12, wherein an amount of the transition metal catalyst complex of from 0.001 mol % to 20 mol %, calculated as transition metal and based on the amount of compound (II.a) or (II.b), is used.

14. The process according to claim 1, wherein the least one monodentate ligand is selected from the group consisting of organo phosphines, organo phosphites, organo phosphonites, organo phosphinites and organo phosphoramidites.

15. The process according to claim 14, wherein the at least one monodentate ligand comprises at least one ligand of formula (IV)

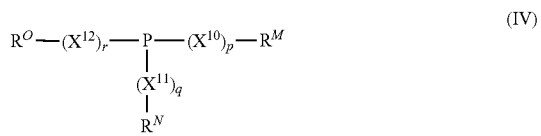

(IV)

wherein $R^M$, $R^N$ and $R^O$ are independently from each other alkyl, cycloalkyl, heterocycloalkyl, aryl or hetaryl, wherein the alkyl radicals may carry 1, 2, 3, 4 or 5 substituents selected from cycloalkyl, heterocycloalkyl, aryl, hetaryl, alkoxy, cycloalkoxy, heterocycloalkoxy, aryloxy, hetaryloxy, hydroxy, mercapto, polyalkylene oxide, polyalkyleneimine, carboxyl, $SO_3H$, sulfonate, $NE^1E^2$, $NE^1E^2E^{3+}X^-$, halogen, nitro, formyl, acyl and cyano, wherein $E^1$, $E^2$ and $E^3$ are the same or different and are selected from hydrogen, alkyl, cycloalkyl, and aryl and X is an anion equivalent, and awherein the radicals cycloalkyl, heterocycloalkyl, aryl and hetaryl $R^M$, $R^N$ and $R^O$ may carry 1, 2, 3, 4 or 5 substituents selected from alkyl and the substituents mentioned for the alkyl radicals RG, RH and RI before, or $R^M$ and $R^N$ or $R^N$ and $R^O$ together with the P atom and, if present, the groups $X^{10}$ $X^{11}$ and $X^{12}$ to which they are bound, are a 5-to 8-membered heterocycle which is optionally fused with one, two or three groups selected from cycloalkyl, heterocycloalkyl, aryl and heteroaryl, wherein the heterocycle and, if present, the fused-on groups independently from each other may each carry 1, 2, 3 or 4 substituents selected from alkyl, cycloalkyl, heterocycloalkyl, aryl, hetaryl, hydroxy, mercapto, polyalkylene oxide, polyalkyleneimine, alkoxy, halogen, carboxyl, $SO_3H$, sulfonate, $NE^4E^5$, $NE^4E^5E^{6+}X^-$, nitro, alkoxycarbonyl, formyl, acyl and cyano, wherein $E^4$, $E^5$ and $E^6$ are the same or different and are selected from hydrogen, alkyl, cycloalkyl and aryl and X is an anion equivalent, $X^{10}$, $X^{11}$ and $X^{12}$ are independently from each other O, S, $CR^xR^y$, $SiR^xR_y$, or $NR^z$, wherein $R^x$, $R^y$ and $R^z$ are independently from each other hydrogen, alkyl, cycloalkyl, heterocycloalkyl, aryl or hetaryl, p, q and r are independently from each other 0 or 1.

16. The process according to claim 15, where the least one monodentate ligand is selected from the group consisting of triphenylphosphine, tris(p-tolyl)phosphine, tris(4-methoxyphenyl)phosphine, tris(4-trifluoromethylphenyl)phosphine, tris(o-tolyl)phosphine, triphenylphosphite and trimethylphosphite.

17. The process according to claim 1, wherein the molar ratio of the transition metal catalyst complex to the least one monodentate ligand is in the range of 1:3.0 to 1:1.2.

18. The process according to claim 17, wherein the molar ratio of the transition metal catalyst complex to the at least one monodentate ligand is in the range of 1:2.5 to 1:1.3.

19. The process according to claim 1, wherein at least one Lewis acid is selected from the group consisting of Al$(OTf)_3$, Sc$(OTf)_3$, Fe$(OTf)_3$, Yb$(OTf)_3$, Eu$(OTf)_3$, B$(C_6F_5)_3$, B$(2,4-(CF_3)_2C_6H_3)_3$, $BF_3$, $BF_3$*$Et_2O$, $BF_3$*THF, Ag(OTf), Pr$(OTf)_3$ and Zn$(OTf)_3$.

20. The process according to claim 1, wherein the polydentate ligand is tris(diphenylphosphinomethyl)methane and the monodentate ligand is triphenylphosphite.

21. The process according to claim 1, wherein each $R^1$ in formula (I) is selected from $C_1$-$C_{20}$ alkyl, which is unsubstituted or substituted with 1, 2, 3, 4 or 5 substituents selected from OH, halogen, $C_1$-$C_6$ alkoxy and $C_6$-$C_{10}$ aryl.

22. The process according to claim 1, wherein each $R^1$ in formula (I) is selected from $C_1$-$C_6$ alkyl which is unsubstituted or substituted with 1, 2, 3 or 4 substituents selected from OH, halogen and $C_1$-$C_4$ alkoxy.

23. The process according to claim 1, wherein each $R^1$ in formula (I) is selected from $C_1$-$C_4$ alkyl, which is unsubstituted or substituted with 1 or 2 substituted selected from OH and halogen.

24. The process according to claim 1, wherein each $R^1$ in formula (I) is selected from $C_1$-$C_4$ alkyl, which is unsubstituted.

25. A mixture comprising the least one polydentate ligand and at least one monodentate ligand as defined in claim 1, wherein the molar ratio of polydentate ligand to the at least one monodentate ligand is in the range of 1:5.0 to 1:1.1.

* * * * *